(12) United States Patent
Barringer

(10) Patent No.: US 9,808,494 B2
(45) Date of Patent: Nov. 7, 2017

(54) PROCESS FOR THE EXTRACTION OF CANNABINOIDS FROM CANNABIS USING LIPIDS AS AN EXTRACTION SOLVENT

(71) Applicant: Rm3 Labs LLC, Boulder, CO (US)

(72) Inventor: Ian Barringer, Boulder, CO (US)

(73) Assignee: RM3 Labs, LLC, Boulder, CO (US)

( * ) Notice: Subject to any disclaimer, the term of this patent is extended or adjusted under 35 U.S.C. 154(b) by 47 days.

(21) Appl. No.: 15/004,861

(22) Filed: Jan. 22, 2016

(65) Prior Publication Data

US 2016/0213720 A1    Jul. 28, 2016

Related U.S. Application Data

(60) Provisional application No. 62/106,520, filed on Jan. 22, 2015.

(51) Int. Cl.
  *A01N 65/00* (2009.01)
  *A61K 36/185* (2006.01)

(52) U.S. Cl.
  CPC ........ *A61K 36/185* (2013.01); *A61K 2236/00* (2013.01)

(58) Field of Classification Search
  CPC ..................................................... A61K 36/00
  USPC ........................................................ 424/725
  See application file for complete search history.

(56) References Cited

U.S. PATENT DOCUMENTS

2015/0126754 A1\* 5/2015 Fernandez Cid ...... A61K 31/35
549/391

\* cited by examiner

*Primary Examiner* — Michael Meller
(74) *Attorney, Agent, or Firm* — Dean E. Wolf, Esq.

(57) ABSTRACT

Processes are described herein for the extraction of cannabinoids from cannabis using lipids as an extraction solvent.

12 Claims, 5 Drawing Sheets

PROCESS FOR THE EXTRACTION OF CANNABINOIDS FROM CANNABIS USING LIPIDS AS AN EXTRACTION SOLVENT

RELATED APPLICATION DATA

The present application claims benefit, pursuant to the provisions of 35 U.S.C. §119, of U.S. Provisional Application Ser. No. 62/106,520, titled "PROCESS FOR THE EXTRACTION OF CANNABINOIDS FROM CANNABIS USING LIPIDS AS AN EXTRACTION SOLVENT", naming Ian Barringer as inventor, and filed Jan. 22, 2015, the entirety of which is incorporated herein by reference for all purposes.

DETAILED DESCRIPTION OF EXAMPLE EMBODIMENTS

Overview

Figure 1:
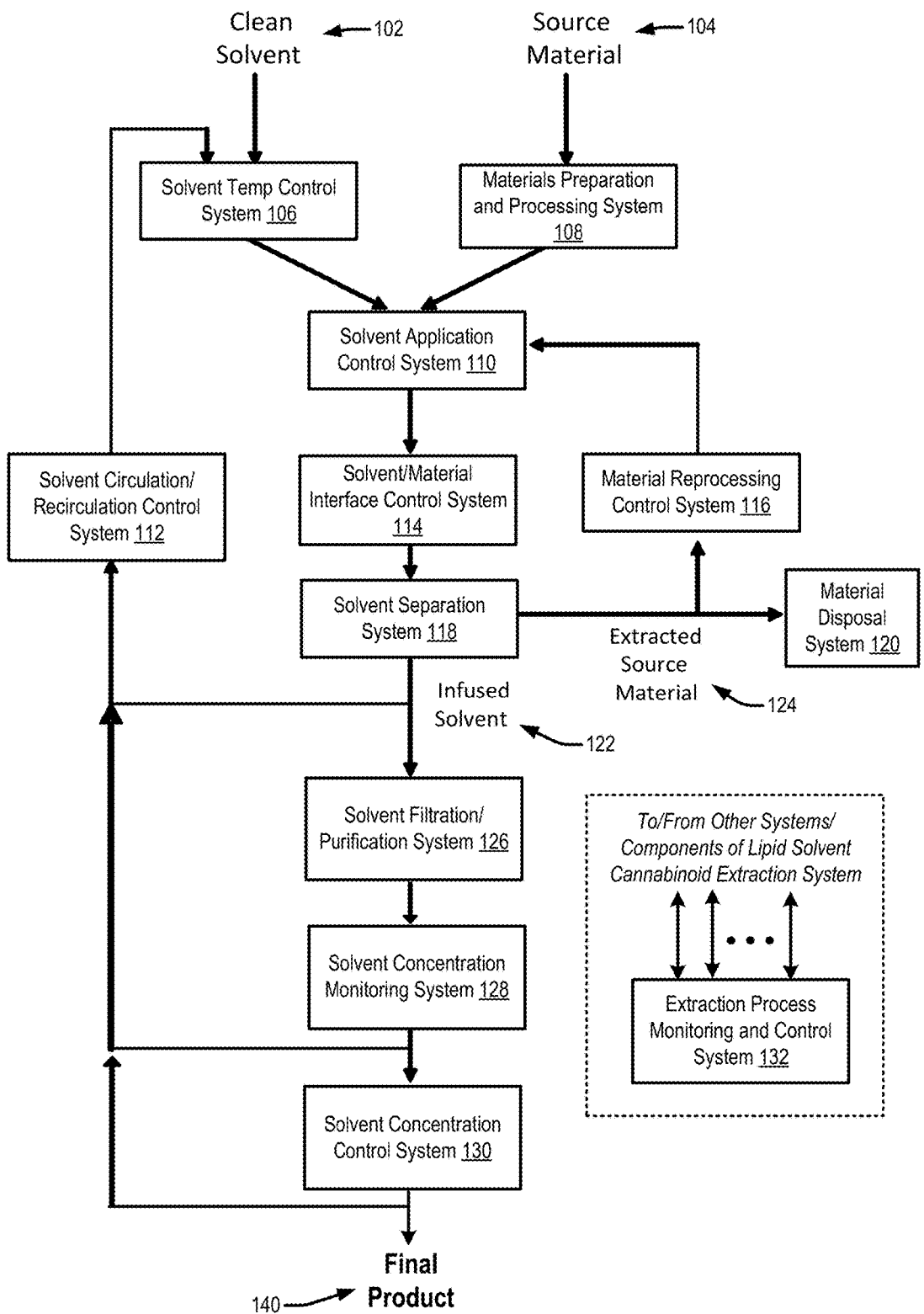
FIG. 1 shows a high level system diagram generally illustrating various component(s) and system(s) which form part of a Lipid Solvent Cannabinoid Extraction System 100

Various aspects described or referenced herein are directed to different methods, systems, and computer program products for extraction of cannabinoids from cannabis using lipids as an extraction solvent. Various objects, features and advantages of the various aspects described or referenced herein will become apparent from the following descriptions of its example embodiments, which descriptions should be taken in conjunction with the accompanying drawings.

Specific Example Embodiments

Various techniques will now be described in detail with reference to a few example embodiments thereof as illustrated in the accompanying drawings. In the following description, numerous specific details are set forth in order to provide a thorough understanding of one or more aspects and/or features described or reference herein. It will be apparent, however, to one skilled in the art, that one or more aspects and/or features described or reference herein may be practiced without some or all of these specific details. In other instances, well known process steps and/or structures have not been described in detail in order to not obscure some of the aspects and/or features described or reference herein.

One or more different inventions may be described in the present application. Further, for one or more of the invention(s) described herein, numerous embodiments may be described in this patent application, and are presented for illustrative purposes only. The described embodiments are not intended to be limiting in any sense. One or more of the invention(s) may be widely applicable to numerous embodiments, as is readily apparent from the disclosure. These embodiments are described in sufficient detail to enable those skilled in the art to practice one or more of the invention(s), and it is to be understood that other embodiments may be utilized and that structural, logical, software, electrical and other changes may be made without departing from the scope of the one or more of the invention(s). Accordingly, those skilled in the art will recognize that the one or more of the invention(s) may be practiced with various modifications and alterations. Particular features of one or more of the invention(s) may be described with reference to one or more particular embodiments or figures that form a part of the present disclosure, and in which are shown, by way of illustration, specific embodiments of one or more of the invention(s). It should be understood, however, that such features are not limited to usage in the one or more particular embodiments or figures with reference to which they are described. The present disclosure is neither a literal description of all embodiments of one or more of the invention(s) nor a listing of features of one or more of the invention(s) that must be present in all embodiments.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. To the contrary, a variety of optional components are described to illustrate the wide variety of possible embodiments of one or more of the invention(s).

Further, although process steps, method steps, algorithms or the like may be described in a sequential order, such processes, methods and algorithms may be configured to work in alternate orders. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred.

When a single device or article is described, it will be readily apparent that more than one device/article (whether or not they cooperate) may be used in place of a single device/article. Similarly, where more than one device or article is described (whether or not they cooperate), it will be readily apparent that a single device/article may be used in place of the more than one device or article.

The functionality and/or the features of a device may be alternatively embodied by one or more other devices that are not explicitly described as having such functionality/features. Thus, other embodiments of one or more of the invention(s) need not include the device itself.

Techniques and mechanisms described or reference herein will sometimes be described in singular form for clarity. However, it should be noted that particular embodiments include multiple iterations of a technique or multiple instantiations of a mechanism unless noted otherwise.

Recent efforts in the field of cannabinoid extraction from plant materials have largely been directed towards the creation of cannabinoid extracts of high purity. In some embodiments, isolation of a single cannabinoid (out of more than 80 identified natural cannabinoids), may be desired.

Many of the developments have focused on the use of liquid or supercritical carbon dioxide as a solvent, either alone or with one or more co-solvents. See, for example, Elsohly et al. (2004), U.S. Pat. No. 6,730,519; and Flockhart et al. (2010) U.S. Pat. No. 7,700,368, each of which is herein incorporated by reference in its entirety for all purposes. These production methods are largely directed towards inclusion of the resulting cannabinoid preparations in pharmaceutical products.

Such production methods tend to involve hazardous solvents, such as butane, or, in the case of supercritical carbon dioxide extraction, are capital intensive due to the high pressures involved. Both these limitations make these technologies difficult and/or expensive to scale.

By contrast, the growth of the medical marijuana market in the United States and in other nations has led to demand for lower-cost, safer extraction methods. For many medical marijuana preparations, the retention of the full mix of cannabinoids present in the cannabinoid-bearing material is desirable. In addition, it may be desirable to retain certain of the terpenoid or phenolic compounds found in marijuana, which give the product is characteristic smell and which, in many cases, may themselves have physiological activity. For certain medical marijuana products, extraction of limited levels of these non-cannabinoids may be desirable, rather than a flaw.

The legal marijuana markets have also seen exceptionally high popularity of non-smoked products, particularly edibles but also capsules and other nontraditional preparations. To make these products, cannabinoids are generally first extracted from the plant material before being incorporated into the end products. Traditionally, separations have been done by mechanical means, where cannabinoid-containing trichomes are broken off the plant material (kief, bubble hash) or with solvents such as butane or, more recently, carbon dioxide.

Lipids have also been used in traditional preparations, most notably in making "cannabutter", where the butter serves as a solvent. Such methods generally require prolonged steeping of the plant material, often for 24 hours or more, at temperatures up to 240 degrees Fahrenheit. Such preparations generally yield less than 10 milligrams of cannabinoids per milliliter of solvent, and generally include significant levels of chlorophyll and other undesirable compounds.

Various aspects disclosed herein are directed to novel cannabinoid extraction techniques which allow for the rapid extraction of substantially all cannabinoids (e.g., greater than 95% of cannabinoids) in plant material, in a format suitable for immediate inclusion in edible products, capsules and similar preparations. Depending on the desired outcome and the quality of the cannabinoid-bearing material, extracts containing in excess of 30 milligrams of cannabinoids per milliliter of solvents may be obtained.

One aspect disclosed herein is directed a process for the extraction of cannabinoids from plant or other materials (the "cannabinoid-bearing material" or "source material") using a lipid solvent and a relatively short contact period (e.g., 30-120 minutes) in order to yield commercially desirable cannabinoid extracts. This method takes advantage of the fact that the majority of cannabinoids in raw plant materials is found on the surface of the material.

Freshly harvested or dried plant material may be used as a source material. Certain low-grade extracts and other cannabinoid-bearing materials may also be processed with this method.

Prior to extraction, the cannabinoid-bearing material may be heated or otherwise treated to convert acidic cannabinoids in the cannabinoids to their neutral forms, which generally have greater physiological activity.

To the extent necessary, the cannabinoid-bearing material is first processed to remove stems, stalks, seeds or other material other than leaves and flowering buds. Such processing may be minimized in order to avoid breakage of cellular membranes in the cannabinoid-bearing material, which may increase the level of non-cannabinoid compounds, particularly chlorophyll, in the end product.

In a preferred embodiment, a vegetable oil that is liquid at room temperature is used as the extraction solvent. In order to minimize the extraction of chlorophyll and other undesired compounds, the solvent is kept relatively cool—less than 180 degrees Fahrenheit—and contact between the cannabinoid-bearing material and the solvent is generally limited to twelve hours or less.

In some embodiments, the combined cannabinoid-bearing material and solvent may be agitated during this period. Such agitation may be accomplished through the natural action of the machinery employed, such as the movement of the cannabinoid-bearing material/solvent mixture through a feed auger, or may be achieved through such nondisruptive methods as shaking or low-intensity ultrasound.

The solvent and cannabinoid-bearing material may be combined either before or after entry of the cannabinoid-bearing material into the separating machinery. In one embodiment, the solvent may be introduced to the cannabinoid-bearing material in an auger conveying the cannabinoid-bearing material from a containment bin to the separating machinery. In another embodiment, the solvent may be sprayed on the cannabinoid-bearing material as the material enters a centrifugal separator or belt press. In either case, the time between combination and separation (the "latency period") is carefully controlled.

Temperature may also be controlled during the latency period. Accordingly, the solvent is heated or chilled before it is introduced to the cannabinoid-bearing material. In one embodiment, the solvent is warmed to approximately 140 degrees Fahrenheit.

Traditional steeping methods typically require soaking of plant material in vegetable oil or butter at temperatures of 200 to 240 degrees Fahrenheit for periods of 24 to 72 hours. These procedures rely on the slow diffusion of cannabinoids from the plant product into the oil or butter.

In contrast, the Lipid Solvent Cannabinoid Extraction techniques described herein adjust and control various parameters relating to the temperature, pressure and flow rate of the solvent through the plant material to thereby dissolve the cannabinoids of the source material in significantly shorter time, and yielding significantly higher quality extracts.

Benefits/Advantages of the Lipid Solvent Cannabinoid Extraction techniques described herein may include, but are not limited to, one or more of the following (or combinations thereof):

- it is materially safer than extractions using butane or other hydrocarbons or alcohols;
- it is significantly less expensive and more efficient than extractions using carbon dioxide as a solvent;
- it can be performed using certified organic solvents;
- it is faster and safer than traditional steeping methods using butter or vegetable oil;
- it is capable of producing significantly more potent end products than traditional steeping methods;
- etc.

Figure 3:
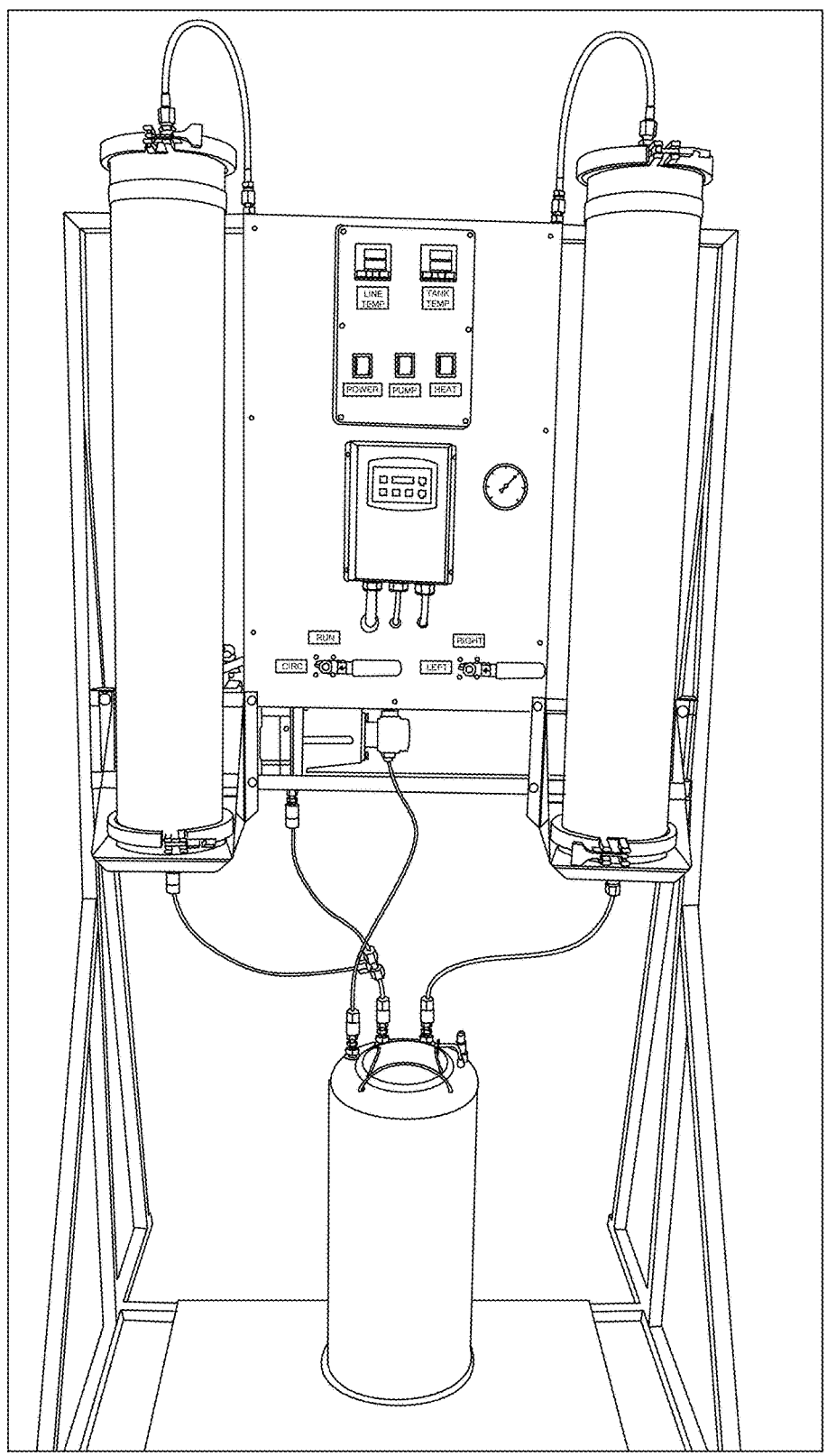
FIG. 3 shows an image of a Lipid Solvent Cannabinoid Extraction apparatus which may be used for implementing Lipid Solvent Cannabinoid Extraction processes described herein.

FIG. 3 shows an image of a Lipid Solvent Cannabinoid Extraction apparatus which may be used for implementing Lipid Solvent Cannabinoid Extraction processes described herein.

Figure 4:
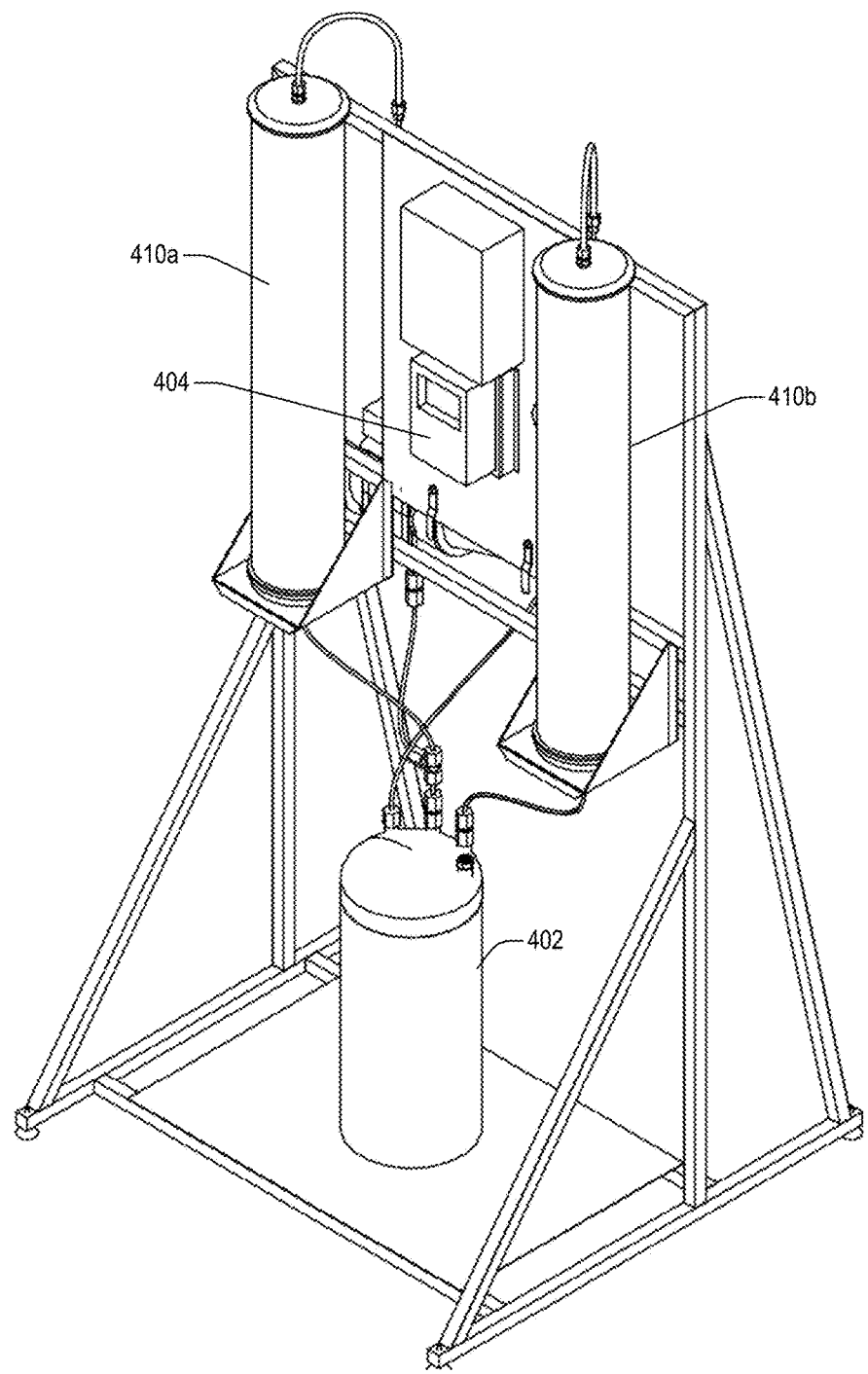
FIG. 4 shows a schematic diagram of a Lipid Solvent Cannabinoid Extraction apparatus 400 which may be used for implementing Lipid Solvent Cannabinoid Extraction processes described herein.

FIG. 4 shows a schematic diagram of a Lipid Solvent Cannabinoid Extraction apparatus 400 which may be used for implementing Lipid Solvent Cannabinoid Extraction processes described herein. As illustrated in the example embodiment of FIG. 4, one or more extraction chambers (e.g., 410a, 410b) may be provided for conducting Lipid Solvent Cannabinoid Extraction on source material. In the specific example embodiment of FIG. 4, container 402 is the Lipid Solvent reservoir. In this particular example embodiment, the output Lipid Solvent (e.g., from extraction chambers 410a, 410b) may be returned to the reservoir container 402 and recirculated to extraction chambers 410a, 410b until it is determined that extraction complete. In other embodiments (not shown) at least one additional reservoir container may be provided to receive the output (e.g., infused) solvent. In such alternate embodiments, at least one reservoir container may be configured or designed to store non-infused solvent, and at least one other reservoir container may be configured or designed to store infused solvent (e.g., output solvent from extraction chamber(s)). In some embodiments, a timer system (e.g., 404) may be used to control one or more timing-related aspects of the Lipid Solvent Cannabinoid Extraction process, such as, for example, controlling ending or termination of a given Lipid Solvent Cannabinoid Extraction process.

Figure 5:
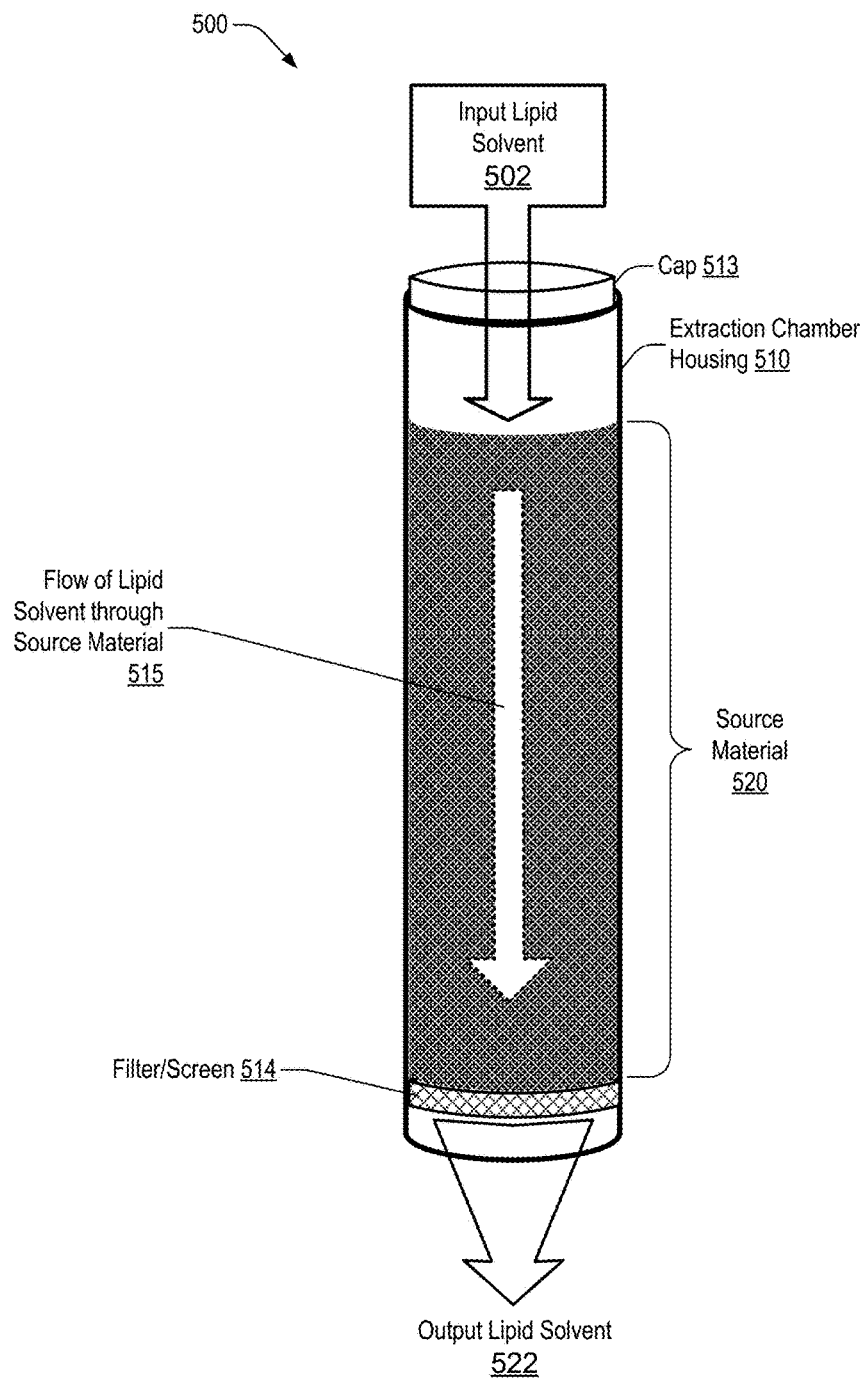
FIG. 5 shows a schematic diagram of an example extraction chamber 500 where Lipid Solvent Cannabinoid Extraction is being performed.

FIG. 5 shows a schematic diagram of an example extraction chamber 500 where Lipid Solvent Cannabinoid Extraction is being performed. As illustrated in the example embodiment of Figure, Source Material (e.g., 520) may be placed in the internal cavity of Extraction Chamber Housing 510. In one embodiment, the Extraction Chamber Housing dimensions may be about 6" diameter by 36" length. In other embodiments, the extraction chamber may be configured or designed to have dimensions such that the ratio of the internal chamber diameter to the chamber length is about 1:6. Pressurized input Lipid Solvent 502 may be introduced to the internal cavity of Extraction Chamber Housing 510. Cap 513 may be used to provide a sealing mechanism to maintain the pressure, and prevent leakage of solvent. The input solvent is forced (e.g., by the pressurized environment) to flow through the source material 510 (as indicated at 515). As the lipid solvent interacts with the source material, the solvent becomes infused with cannabinoids from the source material. The infused lipid solvent 522 (also referred to as output lipid solvent) exits the source material as shown at 522. As illustrated in the example embodiment of FIG. 5, a filter or screen 514 may be employed to allow the output lipid solvent to flow out of source material, while preventing any source material from escaping from the extraction chamber. In some embodiments, the output lipid solvent may be recirculated during the extraction process, and introduced as input lipid solvent. In other embodiments, the output lipid solvent may be collected and not recirculated.

Example System and Flow Diagrams

Figure 2:
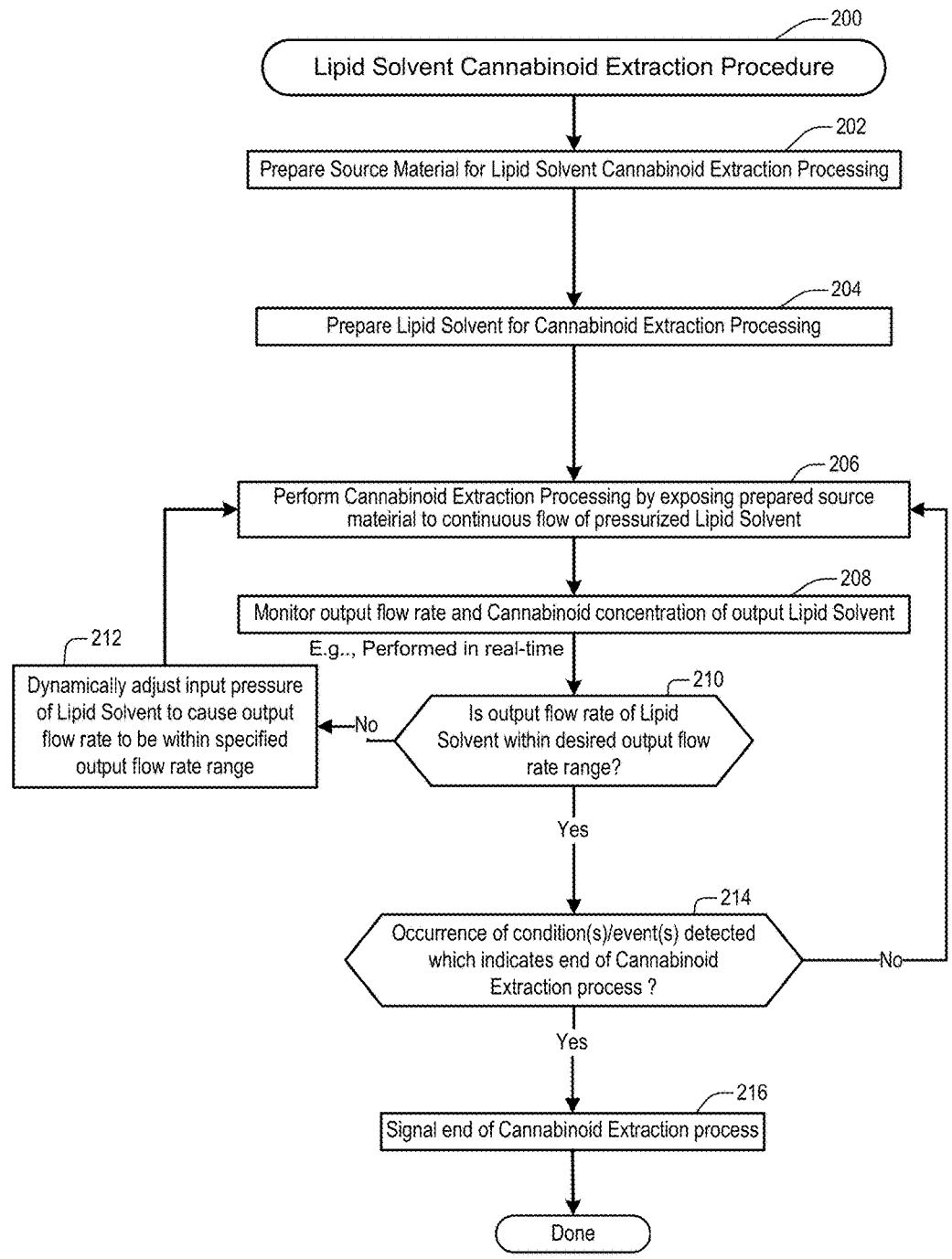
FIG. 2 shows a flow diagram of a Lipid Solvent Cannabinoid Extraction Procedure in accordance with a specific embodiment.

FIGS. 1 and 2 illustrate various example embodiments of different Lipid Solvent Cannabinoid Extraction systems and procedural flows which may be used for facilitating activities relating to one or more of the Lipid Solvent Cannabinoid Extraction aspects disclosed herein.

In at least one embodiment, one or more of the Lipid Solvent Cannabinoid Extraction system(s)/procedure(s) may be operable to utilize and/or generate various different types of data and/or other types of information when performing specific tasks and/or operations. This may include, for example, input data/information and/or output data/information. For example, in at least one embodiment, the Lipid Solvent Cannabinoid Extraction system(s)/procedure(s) may be operable to access, process, and/or otherwise utilize information from one or more different types of sources, such as, for example, one or more local and/or remote memories, devices and/or systems. Additionally, in at least one embodiment, the Lipid Solvent Cannabinoid Extraction system(s)/procedure(s) may be operable to generate one or more different types of output data/information, which, for example, may be stored in memory of one or more local and/or remote devices and/or systems. Examples of different types of input data/information and/or output data/information which may be accessed and/or utilized by the Lipid Solvent Cannabinoid Extraction system(s)/procedure(s) may include, but are not limited to, one or more of those described and/or referenced herein.

In at least one embodiment, a given instance of the Lipid Solvent Cannabinoid Extraction system(s)/procedure(s) may access and/or utilize information from one or more associated databases. In at least one embodiment, at least a portion of the database information may be accessed via communication with one or more local and/or remote memory devices. Examples of different types of data which may be accessed by the Lipid Solvent Cannabinoid Extraction system(s)/procedure(s) may include, but are not limited to, one or more of those described and/or referenced herein.

According to specific embodiments, multiple instances or threads of the Lipid Solvent Cannabinoid Extraction system(s)/procedure(s) may be concurrently implemented and/or initiated via the use of one or more processors and/or other combinations of hardware and/or hardware and software. For example, in at least some embodiments, various aspects, features, and/or functionalities of the Lipid Solvent Cannabinoid Extraction system(s)/procedure(s) may be performed, implemented and/or initiated by one or more of the various systems, components, systems, devices, system(s)/procedure(s), processes, etc., described and/or referenced herein.

According to different embodiments, one or more different threads or instances of the Lipid Solvent Cannabinoid Extraction system(s)/procedure(s) may be initiated in response to detection of one or more conditions or events satisfying one or more different types of threshold criteria for triggering initiation of at least one instance of the Lipid Solvent Cannabinoid Extraction system(s)/procedure(s). Various examples of conditions or events which may trigger initiation and/or implementation of one or more different threads or instances of the Lipid Solvent Cannabinoid Extraction system(s)/procedure(s) may include, but are not limited to, one or more of those described and/or referenced herein.

Similarly, one or more different threads or instances of the Lipid Solvent Cannabinoid Extraction system(s)/procedure(s) may be ended or terminated in response to detection of one or more conditions or events satisfying one or more different types of threshold criteria for triggering the ending or termination of at least one active instance of the Lipid Solvent Cannabinoid Extraction system(s)/procedure(s). Various examples of conditions or events which may trigger the ending or termination of one or more different threads or instances of the Lipid Solvent Cannabinoid Extraction system(s)/procedure(s) may include, but are not limited to, one or more of those described and/or referenced herein.

According to different embodiments, one or more different threads or instances of the Lipid Solvent Cannabinoid Extraction system(s)/procedure(s) may be initiated and/or implemented manually, automatically, statically, dynamically, concurrently, and/or combinations thereof. Additionally, different instances and/or embodiments of the Lipid Solvent Cannabinoid Extraction system(s)/procedure(s) may be initiated at one or more different time intervals (e.g., during a specific time interval, at regular periodic intervals, at irregular periodic intervals, upon demand, etc.).

In at least one embodiment, initial configuration of a given instance of the Lipid Solvent Cannabinoid Extraction system(s)/procedure(s) may be performed using one or more different types of initialization parameters. In at least one embodiment, at least a portion of the initialization parameters may be accessed via communication with one or more local and/or remote memory devices. In at least one embodiment, at least a portion of the initialization parameters provided to an instance of the Lipid Solvent Cannabinoid Extraction system(s)/procedure(s) may correspond to and/or may be derived from the input data/information.

FIG. 1 shows a high level system diagram generally illustrating various component(s) and system(s) which form part of a Lipid Solvent Cannabinoid Extraction System 100. According to different embodiments, the Lipid Solvent Cannabinoid Extraction System 100 may include a plurality of different types of components, devices, modules, processes, systems, etc., which, for example, may be implemented and/or instantiated via the use of hardware and/or combinations of hardware and software. For example, as illustrated in the example embodiment of FIG. 1, the Lipid Solvent Cannabinoid Extraction System 100 may include one or more of the following types of systems, components, devices, processes, etc. (or combinations thereof):

Extraction Process Monitoring and Control System 132, which, for example, may be configured or designed to provide automated functionality for managing and/or handling various aspects of the Lipid Solvent Cannabinoid Extraction process relating to extraction process monitoring and control, and control/management of one or more of the various sub-systems of the Lipid Solvent Cannabinoid Extraction System.

Solvent Temp Control System 106, which, for example, may be configured or designed to provide automated functionality for handling various aspects of the Lipid Solvent Cannabinoid Extraction process relating to solvent temperature monitoring and control.

Materials Preparation and Processing System 108, which, for example, may be configured or designed to provide automated functionality for handling various aspects of the Lipid Solvent Cannabinoid Extraction process relating to materials preparation and processing.

Solvent Application Control System 110, which, for example, may be configured or designed to provide automated functionality for handling various aspects of the Lipid Solvent Cannabinoid Extraction process relating to solvent application control.

Solvent/Material Interface Control System 114, which, for example, may be configured or designed to provide automated functionality for handling various aspects of the Lipid Solvent Cannabinoid Extraction process relating to solvent/material interface control.

Solvent Separation System 118, which, for example, may be configured or designed to provide automated functionality for handling various aspects of the Lipid Solvent Cannabinoid Extraction process relating to solvent separation from source material.

Solvent Filtration/Purification System 126, which, for example, may be configured or designed to provide automated functionality for handling various aspects of the Lipid Solvent Cannabinoid Extraction process relating to solvent filtration/purification.

Solvent Concentration Monitoring System 128, which, for example, may be configured or designed to provide automated functionality for handling various aspects of the Lipid Solvent Cannabinoid Extraction process relating to solvent concentration monitoring.

Solvent Concentration Control System 130, which, for example, may be configured or designed to provide automated functionality for handling various aspects of the Lipid Solvent Cannabinoid Extraction process relating to solvent concentration control (e.g., including dilution of Solvent to achieve Final Product).

Material Reprocessing Control System 116, which, for example, may be configured or designed to provide automated functionality for handling various aspects of the Lipid Solvent Cannabinoid Extraction process relating to Source Material reprocessing control (e.g., reprocessing of source material to achieve additional cannabinoid extraction).

Material Disposal System 120, which, for example, may be configured or designed to provide automated functionality for handling various aspects of the Lipid Solvent Cannabinoid Extraction process relating to Source Material disposal.

Solvent Circulation/Recirculation Control System 112, which, for example, may be configured or designed to provide automated functionality for handling various aspects of the Lipid Solvent Cannabinoid Extraction process relating to solvent circulation/recirculation monitoring and control.

Solvent Pressure Monitoring and Control System 115, which, for example, may be configured or designed to provide automated functionality for handling various aspects of the Lipid Solvent Cannabinoid Extraction process relating to solvent pressure monitoring and control.

Solvent Flow Rate Monitoring and Control System 117, which, for example, may be configured or designed to provide automated functionality for handling various aspects of the Lipid Solvent Cannabinoid Extraction process relating to solvent flow rate monitoring and control.

Timer control system 133, which, for example, may be configured or designed to provide automated functionality for handling various aspects of the Lipid Solvent Cannabinoid Extraction process relating to timer control of the Lipid Solvent Cannabinoid Extraction Procedure and sub-procedures thereof.

Extraction Process Endpoint Detection System 135, which, for example, may be configured or designed to provide automated functionality for handling various aspects of the Lipid Solvent Cannabinoid Extraction process relating to extraction process endpoint detection.

FIG. 2 shows a flow diagram of a Lipid Solvent Cannabinoid Extraction Procedure in accordance with a specific embodiment. According to different embodiments, at least a portion of the various types of functions, operations, actions, and/or other features provided by the Lipid Solvent Cannabinoid Extraction Procedure of FIG. 2 may be implemented at one or more systems of the Lipid Solvent Cannabinoid Extraction System 100 of FIG. 1.

As illustrated at 202, prepare source material for lipid solvent Cannabinoid extraction processing, which, for example, may include, but are not limited to, one or more of the following (or combinations thereof):
  Acquire desired quantity of Source Material (e.g., 10 lbs.)
  Dry Source Material
  Crush/Grind Source Material into desired granularity (e.g., approx. ¼ inch particles)
  Place prepared Source Material into Extraction Container
  Etc.

As illustrated at 204, the system may prepare lipid solvent for Cannabinoid extraction processing, which, for example, may include, but are not limited to, one or more of the following (or combinations thereof):
  Acquire desired type/quantity of Lipid Solvent
  Heat to desired temperature (e.g., 140 degrees F.).
  Pressurize to desired initial pressure value
  Set desired flow rate parameters
  Etc.

As illustrated at 206, the system may perform Cannabinoid extraction processing by exposing prepared source material to continuous flow of pressurized lipid solvent As illustrated at 208, the system may continuously and/or periodically monitor output flow rate and Cannabinoid concentration of output lipid solvent. In at least some embodiments, such monitoring may be performed in real-time or substantially real-time.

As illustrated at 210, the system may determine if the output flow rate of lipid solvent within desired output flow rate (or flow rate range), such as, for example, Desired Output Flow Rate Range=1-3 liters per minute, Desired flow rate=2 liters per minute.

As illustrated at 212, if it is determined that the output flow rate of the lipid solvent is not within a desired output flow rate range, the system may automatically and/or dynamically adjust input pressure of Lipid Solvent to cause output flow rate to be within specified output flow rate range As illustrated at 214, the system may continuously and/or periodically monitor conditions of the extraction process to detect occurrence(s) of condition(s)/event(s) which indicate an end of the Cannabinoid Extraction process. Examples of such ending condition(s)/event(s) may include, but are not limited to, one or more of the following (or combinations thereof):
  Cannabinoid concentration of output Lipid Solvent is at target concentration value, such as, for example, Target Cannabinoid Concentration Range=0-50 mg/ml, preferred target Cannabinoid Concentration Range=15 mg/ml to 30 mg/ml, etc.
  Predetermined time interval has elapsed (e.g., timer expired), such as, for example, Processing Range: 10 mins to 8 hours, preferred target processing time=2 hours, etc.
  Etc.

As illustrated at 216, when the system detects at least one condition/event indicating an end of the extraction process, the system may signal end of Cannabinoid Extraction process, and, in some embodiments, may automatically and dynamically initiate actions to halt or terminate the extraction process.

By way of illustration, the following provides example parameters/values of one embodiment of a Lipid Solvent Cannabinoid Extraction Procedure:
  Extraction mechanism: controlled flow of solvent through a packed column of plant material.
  Extraction container dimensions: 6" diameter by 36" length, with an aspect ratio of 6:1;
  Material 6 to 12 lbs. dried plant material, containing 10% cannabinoids by dry weight;
  Solvent: 4.5 gallons;
  Solvent type: vegetable oil such as safflower oil, coconut oil, etc.
  Solvent pressure between 3 psi and 15 psi; (e.g., target pressure value=6 psi for medium-fine granularity of source material);
  Temperature of solvent between 100 and 170 degrees Fahrenheit (e.g., 140 degrees F.);
  Solvent flow rate through plant material between 2 and 10 inches per minute; Desired Output Flow Rate Range=1-3 liters per minute. E.g., Desired flow rate=2 liters per minute.
  Solvent is separated from plant material by a screen or filter at the far end of the extraction chamber.
  Resulting extract will contain approximately 15 milligrams of cannabinoids per milliliter using a single chamber, or 33 mg/ml using dual chambers in series.

The solvent may be separated from the cannabinoid-bearing material by filtration, pressing, centrifugal screening or a similar process. Contact between the cannabinoid-bearing material and the solvent, with proper agitation and/or flow rates, may remove 90% or more of the cannabinoids from the cannabinoid-bearing material in 30 minutes or less.

The extraction may be repeated in order to achieve extraction of 95% to 99% of the starting cannabinoids in the cannabinoid-bearing material. This second pass may generally produce tinctures of lower strength than the first pass.

In a further embodiment, the infused solvent may then be filtered or clarified to remove any remaining suspended material from the solvent.

In a further embodiment, part or all of the infused solvent may be "recycled" and introduced to further cannabinoid-bearing material, increasing the cannabinoid content of the final extract.

The infused solvent may be used in the form in which it emerges from the separation process, or diluted to a particular desired strength.

The solvent may be any lipid for which the melting point is of a temperature that may not damage the plant material, generally 300 degrees Fahrenheit or less. Embodiments include canola oil, coconut oil, olive oil, safflower oil, sunflower oil, butter, cocoa butter, shea butter or similar fats. Less common lipids such as fatty acids, monoglycerides, diglycerides, sterols or saccharolipids may also be used. However, cost, stability, and suitability for use in end products may be considered in the selection of the solvent. In the preferred embodiment, the solvent is a vegetable oil that is liquid at room temperature, due to ready availability, significant cannabinoid carrying capacity and the wide range of potential uses.

In a further embodiment, this process may be used for the extraction of desirable soluble components from other source materials in which the desired components are located primarily on the surface of the source material in question.

It will be appreciated that the system and procedural diagrams of FIGS. 1-5 are merely specific examples of system components and/or procedural flows/activities which may be implemented to achieve one or more aspects of the Lipid Solvent Cannabinoid Extraction techniques described herein. Other embodiments of Lipid Solvent Cannabinoid Extraction System(s)/Component(s) (not shown) and/or Lipid Solvent Cannabinoid Extraction Procedural flows (not shown) may include additional, fewer and/or different components, steps, actions, and/or operations than those illustrated in the example embodiments illustrated in FIGS. 1-5.

Other Features/Benefits/Advantages

According to different embodiments, at least some embodiments may be configured, designed, and/or operable to provide, enable and/or facilitate one or more of the following features, functionalities, benefits and/or advantages (or combinations thereof):
- A press or similar mechanism may be incorporated into the extraction chamber to remove as much solvent as possible from the plant material at the end of the extraction process.
- The time, temperature, pressure and other variables involved in the process may be automated or controlled by computer in order to minimize operator training and involvement.
- A second extraction chamber or mechanism can be run in series with the primary chamber to increase the concentration of cannabinoids in the final solvent.

Although several example embodiments of one or more aspects and/or features have been described in detail herein with reference to the accompanying drawings, it is to be understood that aspects and/or features are not limited to these precise embodiments, and that various changes and modifications may be effected therein by one skilled in the art without departing from the scope of spirit of the invention(s) as defined, for example, in the appended claims.

It is claimed:

1. A process for producing a cannabinoid infused fat from cannabis comprising:
    a) placing cannabis in the interior of a column to produce a packed column portion, the packed column portion being configured or designed to permit a flow of liquids through the packed column portion, the packed column portion including a filter or screen to prevent the cannabis from escaping from the interior of the packed column portion while a fat flows through the packed column portion; and
    b) adding a fat to flow through the interior of the packed column portion and to interact with the cannabis, wherein the interaction of the fat and cannabis causes cannabinoids to be extracted from the cannabis and infused into the fat, and wherein separation of the cannabinoid infused fat from the cannabis is achieved by allowing the cannabinoid infused fat to flow out of the interior of the packed column portion, wherein said fat is selected from the group consisting of: cocoa butter, sunflower oil, coconut oil, safflower oil and canola oil.

2. The process in claim 1, further comprising agitating the packed column portion of cannabis and fat with ultrasonic waves to facilitate separation of the fat from the cannabis.

3. The process in claim 1, further comprising agitating the packed column portion of cannabis and fat using a mechanical process to facilitate separation of the fat from the cannabis.

4. The process defined in claim 1, wherein the separating of step c) is less than six hours from when the fat is first introduced to the cannabis.

5. The process defined in claim 1, wherein the separating of step c) is less than one hour from when the fat is first introduced to the cannabis.

6. The process defined in claim 1, wherein the separation of the fat from the cannabis is a continuous process.

7. The process defined in claim 1, wherein the separation of the fat from the cannabis is a periodic, non-continuous process.

8. The process defined in claim 1, wherein the separation of the fat from the cannabis is further achieved via use of a centrifugal separator.

9. The process defined in claim 1, further comprising repeating the extraction process after the cannabis is separated from the fat to extract more cannabinoids from the cannabis.

10. The process defined in claim 1, further comprising adding more cannabis to the packed column portion to thereby increase the cannabinoid concentration of the cannabinoid infused fat.

11. The process defined in claim 1, further comprising filtering or clarifying the cannabinoid infused fat of step c) to remove residual particles of extracted cannabis.

12. The process defined in claim 1, further comprising diluting the cannabinoid infused fat of step c) to yield a dilute cannabinoid infused fat.

* * * * *